United States Patent
Monsalvo Garcia et al.

(10) Patent No.: US 12,077,737 B2
(45) Date of Patent: Sep. 3, 2024

(54) ANAEROBIC PHOTOBIOREACTOR AND METHOD FOR BIOMASS CULTIVATION, WASTEWATER TREATMENT, NUTRIENTS RECOVERY, ENERGY PRODUCTION AND HIGH-VALUE PRODUCTS SYNTHESIS

(71) Applicant: FCC AQUALIA S.A., Madrid (ES)

(72) Inventors: Victor Monsalvo Garcia, Madrid (ES); Daniel Puyol Santos, Madrid (ES); Juan Antonio Melero Hernandez, Madrid (ES); Fernando Martinez Castillejo, Madrid (ES); Raul Molina Gil, Madrid (ES); Zouhayr Arbib, Madrid (ES); Frank Rogalla, Madrid (ES)

(73) Assignee: FCC AQUALIA S.A., Madrid (ES)

( * ) Notice: Subject to any disclaimer, the term of this patent is extended or adjusted under 35 U.S.C. 154(b) by 980 days.

(21) Appl. No.: 17/041,841

(22) PCT Filed: Mar. 27, 2019

(86) PCT No.: PCT/EP2019/057750
§ 371 (c)(1),
(2) Date: Sep. 25, 2020

(87) PCT Pub. No.: WO2019/185734
PCT Pub. Date: Oct. 3, 2019

(65) Prior Publication Data
US 2021/0032581 A1    Feb. 4, 2021

(30) Foreign Application Priority Data

Mar. 27, 2018    (EP) .................................... 18382210

(51) Int. Cl.
*C05F 17/40*    (2020.01)
*C02F 1/30*    (2023.01)
(Continued)

(52) U.S. Cl.
CPC ............... *C12M 21/02* (2013.01); *C02F 1/30* (2013.01); *C02F 3/2866* (2013.01); *C05F 7/005* (2013.01);
(Continued)

(58) Field of Classification Search
None
See application file for complete search history.

(56) References Cited

U.S. PATENT DOCUMENTS 4,654,308 A * 3/1987 Safi ......................... C12M 25/06
312/236
5,162,051 A    11/1992 Hoeksema
(Continued)

FOREIGN PATENT DOCUMENTS

AU    2004/229070 A1 *  6/2005   ............ C12M 1/107
CH    700388 A2    8/2010
(Continued)

OTHER PUBLICATIONS

Hulsen et al., "Domestic wastewater treatment with purple phototrophic bacteria using a novel continuous photo anaerobic membrane bioreactor", Water Research, 2016, vol. 100, pp. 486-495.
(Continued)

*Primary Examiner* — Wayne A Langel
(74) *Attorney, Agent, or Firm* — LUCAS & MERCANTI, LLP

(57) ABSTRACT

The present invention is related to an anaerobic photobioreactor and a method for active biomass cultivation, wastewater treatment, nutrients recovery, energy production and high-value products synthesis. Phototrophic bacteria are cultured in the anaerobic photobioreactor lighted with solar or artificial irradiation where certain light wavelengths are selectively discarded with a light selector installed on the top of the photobioreactor. In this light-based process wastewa-
(Continued)

ter treatment and resources recovery, like nutrients and high-value bioproducts (fertilizers, polymers and proteins) present in wastewater are performed simultaneously. Cultured biomass is treated by anaerobic digestion for biofuel production, including optative hydrolytic pre-treatment, and/or valuable bioproducts can be obtained in a downstream process.

9 Claims, 4 Drawing Sheets

(51) Int. Cl.
*C02F 3/28* (2023.01)
*C05F 7/00* (2006.01)
*C05F 17/30* (2020.01)
*C05F 17/986* (2020.01)
*C12M 1/00* (2006.01)
*C12M 1/107* (2006.01)
*C12M 1/34* (2006.01)

(52) U.S. Cl.
CPC .............. *C05F 17/30* (2020.01); *C05F 17/40* (2020.01); *C05F 17/986* (2020.01); *C12M 21/04* (2013.01); *C12M 23/18* (2013.01); *C12M 23/22* (2013.01); *C12M 23/36* (2013.01); *C12M 23/38* (2013.01); *C12M 31/00* (2013.01); *C12M 41/32* (2013.01); *C12M 41/36* (2013.01); *C12M 41/40* (2013.01); *C12M 43/06* (2013.01); *C12M 45/06* (2013.01); *C12M 47/00* (2013.01); *C02F 2203/006* (2013.01); *C02F 2301/046* (2013.01)

(56) References Cited

U.S. PATENT DOCUMENTS

| | | |
|---|---|---|
| 6,509,188 B1 | 1/2003 | Troesch et al. |
| 8,658,420 B2 | 2/2014 | Gorny et al. |
| 2014/0030695 A1* | 1/2014 | Smith .................... C12M 43/04 |
| | | 435/286.1 |
| 2014/0186909 A1 | 7/2014 | Calzia et al. |

FOREIGN PATENT DOCUMENTS

| | | | |
|---|---|---|---|
| EP | 2875724 A1 | 5/2015 | |
| WO | 2014022689 A1 | 2/2014 | |
| WO | 2014022736 A1 | 2/2014 | |
| WO | WO 2017/211750 A1 * | 12/2017 | .............. C12M 3/00 |

OTHER PUBLICATIONS

Hulsen et al., "Simultaneous treatment and single cell protein production from agri-industrial wastewaters using purple phototrophic bacteria or microalgae—A comparison", Bioresource Technology, 2018, vol. 254, pp. 214-223.

International Search Report and Written Opinion for Corresponding International Application No. PCT/EP2019/057750 (May 29, 2019) (9 Pages).

* cited by examiner

ANAEROBIC PHOTOBIOREACTOR AND METHOD FOR BIOMASS CULTIVATION, WASTEWATER TREATMENT, NUTRIENTS RECOVERY, ENERGY PRODUCTION AND HIGH-VALUE PRODUCTS SYNTHESIS

CROSS REFERENCE TO RELATED APPLICATION

This Application is a 371 of PCT/EP2019/057750 filed on Mar. 27, 2019 which, in turn, claimed the priority of European Patent Application No. 18382210.5 filed on Mar. 27, 2018, both applications are incorporated herein by reference.

FIELD OF THE INVENTION

The present invention is related to anaerobic photobioreactor for wastewater treatment, resources recovery and energy production.

BACKGROUND OF THE INVENTION

Traditionally, biological wastewater treatment is based on the biological oxidation of the organic matter. Drawbacks of this process are the high operation costs associated to oxygen supply, carbon dioxide release and worrisome emission of other greenhouse gases like NOx.

The development of novel biological processes is leading a change in wastewater management strategies for water reuse, as well as, energy and resources recovery contained in wastewater. Carbon footprint minimization and economy optimization are also important challenges.

Anaerobic photobioreactor devices can be enriched in anaerobic purple phototrophic bacteria (PPB) that assimilate soluble organic matter into biomass. Thereby, electron acceptor supply in the form of oxygen, nitrate, sulfate or others is not necessary to remove organics from water. Consequently, chemical energy contained in wastewater as organic matter is efficiently transformed into biomass by using light energy. Then, biofuel (enriched biogas) can be obtained by anaerobic digestion of the PPB biomass produced. PPB biomass is characterized by a high N and P content due to: (a) high protein content associated to the presence of light polypeptides harvesting complexes, and (b) their ability to accumulate P as poly-phosphate. Therefore, PPB-based technologies are a suitable platform for nutrients removal and recovery in aqueous streams.

PPB cultivation in anaerobic photobioreactors represents a feasible solution to provide low-cost wastewater treatment at neutral or even positive energy balance. Energy is produced by coupling assimilation of the organic matter contained in wastewater, biomass production and anaerobic digestion of the resulting biomass. Besides useful resources can be also harvested by nutrients, organics and polymers accumulation in photoactive biomass. Thus, energy (biogas) and high value-added products are obtained in a simultaneous depuration process. Moreover, biomass can be submitted to further downstream process to obtain other useful products as organic NPK fertilizers.

Implementation of photobioreactor technology for wastewater treatment is limited research and development initiatives. The full-scale application of these devices in real environments requires i) to increase the efficiency of light transfer into the bioreactor systems, ii) to develop a proper optimization strategy to increase the system productivity, and iii) to reduce the carbon footprint and operation costs.

The application U.S. Pat. No. 5,162,051A describes a method to cultivate phototrophic microorganisms by using a multiple transparent baffles system located inside the reactor. The light sources are submerged to distribute the light throughout the reactor volume in a homogeneous manner. Its applicability is limited to artificial white light systems, and therefore the use of solar irradiation is discarded.

The patent U.S. Pat. No. 6,509,188B1 describes a method to cultivate algae and other photosynthetic microorganisms by means of an airlift loop reactor/water column illuminated from the side part and can use sun irradiation. Biomass grows on the reactor walls, which hinder the light penetration. This requires a highly turbulent regime by water recirculation and air injection with a high energy consumption. This system can be equipped with wavelength shifters (located on the reactor walls, between the light source and the reactor, or as free particles inside the reaction vessel) to increase the light utilization by the phototrophic biomass. The high installation, operation and maintenance costs hinder the industrial application of this device. These vertical reactors are unable to leverage the full sun radiation, especially during midday, where the sun intensity is maxima. Nevertheless, the culture of anaerobic phototrophic microorganisms, such as purple phototrophic bacteria, is not viable under aerobic conditions.

The patent U.S. Pat. No. 8,658,420B2 describes a multi-wall thermoplastic, flow-through photobioreactor for cultivation of microalgae to produce biofuel. Main advantages of the invention are: no evaporation of water and GHG emission, avoid colonization with external microorganisms, UV filtration, temperature control. Pumping and agitation are not needed, which reduce the operation costs. However, this invention is not feasible for raw wastewater treatment (pre-treatment is necessary), neither high strength wastewater can be treated satisfactorily.

WO2014022689A1 describes a system specifically designed for anaerobic phototrophic bacteria cultivation, using internal illumination by means of LED lamps with emission wavelengths between 700 and 950 nm. The biomass is immobilized in a solid matrix, which allows hydraulic retention time (HRT) and sludge retention time (SRT) decoupling. Market replication of this system has not occurred since it needs artificial illumination, periodical walls cleaning to remove biofilm, and an additional biological system to remove nutrients. WO2014022736A1 describes an invention similar to the WO2014022689A1 patent but focused on the removal and accumulation of phosphorus as poly-phosphate. This is characterized by the same limitations of the WO2014022689A1 patent.

EP2875724A1 describes the use of a high rate algae pond (open raceway) to treat wastewater with concomitant energy recovery in a low-cost industrial system. The system is composed of an open raceway for the cultivation of algae or mixed cultures of aerobic bacteria and algae, where wastewater is circulated with a submerged propulsion system. This invention does not favor the culture of anaerobic phototrophic bacteria since it operates under aerobic conditions and receives solar irradiation (entire spectral range). Instead, this promotes the dominance of algae and other photosynthetic organisms as cyanobacteria.

In resume, existing photobioreactors are optimized for algae and aerobic biomass cultivation, and very few are dedicated to grow phototrophic microorganisms in anaerobic conditions so far. Specifically, there are no inventions where wastewater can be treated with suspended anaerobic PPB at relatively low costs. None of these inventions select the specific spectral range required for PPB biomass cultivation.

The solution proposed by the present invention is a low-cost and highly versatile photobioreactor that optimize the growth of anaerobic phototrophic microorganisms to treat efficiently both high- and low-strength wastewater. This invention can reuse organic compounds, nitrogen, phosphorus, sulfur and other micronutrients presents in the feed to obtain high-value compounds and energy (biogas). This greatly decreases the operation costs and is presented as a fourth-generation technology for wastewater treatment.

SUMMARY OF INVENTION

The present invention is related to an anaerobic photobioreactor for the treatment of wastewater containing organic and inorganic compounds. In a first aspect of the invention, the anaerobic photobioreactor is a horizontal closed anaerobic ditch (101, 201, 301) where the wastewater is fed into the reactor and circulated by using a circulation system (204, 317) as paddle-wheels or other submerged propulsion system.

The integration of the anaerobic photobioreactor in a wastewater treatment plant comprises three main compartments: i) an horizontal closed anaerobic ditch (101, 201, 301), ii) a biomass separator (202, 302), and iii) an anaerobic digester (203, 305), wherein an infrared radiation photo-selective film is placed on the top of the anaerobic photobioreactor over a hermetic lids (103), a circulation system (204, 317) is placed in the anaerobic photobioreactor to keep the biomass in suspension, and a vertical open tube (102) is placed through the hermetic leads.

Furthermore, the horizontal closed anaerobic ditch (101, 201, 301) contains two gas vents (104, 105) to render inert the system if necessary, which are also used as gas sampling point. It also contains a sample tube (102) completely hermetic that is submerged into the liquid and is used to (i) sample the liquid, and (ii) equilibrate the headspace pressure to avoid system overpressure.

The photobioreactor of this invention offers a core unit to treat wastewater and recover resources and energy contained in the feed.

The first aspect of the invention increases the production of PPB biomass in a novel anaerobic photobioreactor, culturing and selecting photobacteria by exposition to infrared light (>750 nm) with a film selector installed on the top of the photobioreactor instead of using aerobic biological process or algae systems. By doing this, the PPB biomass available for the anaerobic digestion step is significantly increased, and photobioreactor overcomes long-standing problems and limitations of this kind of methods (low biomass production, low biological methane production, long HRT and large foot-print), boosting the market replication of light-based biological processes.

The reactor is illuminated from the top part, suitable to use solar irradiation. Artificial irradiation source is also possible in some applications. Remarkable novelties of the system compared to existing raceways for algae cultivation are:

(a) the anaerobic conditions of the system, which are imposed by using covering lids (103) located in the upper part of the photobioreactor and circulation system is hermetically covered;

(b) the existence of a gas headspace between the water line and the covering lids avoids the growth of biofilm on the surface, which limits light dissipation significantly; and (c) the use of a specific radiation filter attained to the reactor lids that reflects and/or absorb all the visible and ultraviolet light (wavelengths below 750 nm), thereby the system is only irradiated with infrared light.

The light may be provided by direct solar irradiation, where solar spectrum is filtrated with a selective filter system and only infrared photons enter into the system. The light can be also provided by a low-energy wavelength-specific light emitting system at wavelengths between 800 and 1050 nm. A combined strategy of natural and artificial light may be also interesting, especially during dark periods.

Another embodiment of the first aspect of the invention, wherein said solar radiation wavelength is selected by installing a selective monochromatic film (750-1200 nm). Artificial IR radiation source can be alternatively used reaching a similar performance. The artificial light system is installed above the anaerobic ditch lids (103), so light is homogeneously distributed along the photobioreactor surface.

Artificial light may be provided at an intensity from 30 to 100 W/m$^2$, depending on the PPB biomass concentration inside the photobioreactor. The biomass concentration and the water column depth in the photobioreactor can be adjusted to optimize light penetration. As a reference value, an average light irradiation of 70 W/m$^2$ is enough to ensure a stable performance of the system working with a water column depth of 40 cm and a biomass concentration of 2 g/L.

Cover lids (103) are used to isolate the bioreactor headspace and operate under anaerobic conditions. This is also useful as support for the infrared light film selector. The lids (103) have two small hermetically closed vents (104, 105) that may be used for (i) nitrogen sparging during the start-up of the process or (ii) maintenance works. Once the reactor is working under steady-state conditions, gas sparging is no longer necessary. The cover lids (103) are made of poly (methyl methacrylate) that absorb ultraviolet light and is 95% transparent to near infrared light.

Another embodiment of the first aspect of the invention, wherein said the covering lids (103) can be made by different synthetic polymers, including (but not exclusively) PMMA with wavelength shifting compounds as aromatic cyano fluorophores, cyanine dyes as 1,1,2-Trimethylbenz-indoleninium 1,3-disulfonate, 5-carboxy-1-(4-sulfobutyl)-2,3,3-trimethyl-3H-indolenine 2, and 1-(4-sulfonatobutyl)-2,3,3-trimethylindoleninium-5-sulfonate, or N-Ethyl-2,3,3-trimethylbenzindoleninium 5,7-Disulfonate.

Main variables to control the operation of the anaerobic reactor are HRT, depth of the water column (DWC), SRT and water circulation rate (WCR). Additionally, in the case of artificial illumination, it is necessary to control the irradiance and the wavelength.

The system can be optimized to treat domestic wastewater (DWW), so that the HRT will depend on the inlet concentration and the biomass concentration inside the system. For typical DWW, HRT between 3 and 24 h are recommended, whereas the biomass concentration is maintained between 0.3 and 3.0 g/L. This essentially means that SRT values should be around 2-8 d depending on the light availability. The WCR will be also linked to the light availability. This system allows a homogeneous biomass distribution along the DWC, which maximizes the incident irradiance and minimizes shaded biomass, so that the light usage by the phototrophic microorganisms will be optimized.

The system is capable of treating wastewater with organic concentrations up to 20 g COD/L.

pH usually remains around 5.5-8.5, although extreme values, i.e. 4.0-9.0, are observed under high irradiation and alkalinity.

The operation of the photobioreactor can be optimized to produce polyhydroxyalkanoates (PHA). The accumulation of these bioplastics is promoted at high substrate concentration and low SRT (around 2 d). Feeds with high organics and low nutrients concentration promote the production of biohydrogen, which can be extracted from the reactor vessel through the gas vents (104, 105). The photobioreactor can be also used to recover sulfur by promoting the growth of photoautotrophic microorganisms. For these purposes, $CO_2$ addition can be necessary by using these gas vents, and an additional gas diffusion system may be necessary.

The photobioreactor can be also used to accumulate phosphorus as poly-phosphate. Dark-light periods or lighten-darken multi-photobioreactors can be used for promoting the accumulation of phosphate. The resulting phosphorus enriched biomass can be used as organic fertilizer. The photobioreactor can be also operated to transform the organics and nitrogen into single-cell proteins-rich biomass that can be used as a valuable byproduct. Other products that can be extracted from the phototrophic organisms are pigments like carotenoids and bacteriochlorophylls.

The biomass inside the system is mainly composed of anaerobic phototrophic bacteria, especially purple non-sulfur bacteria, purple sulfur bacteria and green sulfur bacteria. The biomass can be enriched directly by using the wastewater as inoculum source, thereby no inoculum is necessary for the start-up of the process. Alternatively, a specialized inoculum can be added into the photobioreactor for speeding up the start-up period. Inoculum sources can be domestic waste sludge, lake muds, river muds or artificial enrichments.

Moreover, the efficient organic matter conversion into biomass where a biomass yield close to 99.9% of the maximum theoretical organic matter conversion is reached from the first hours of operation. First, photoactive bacteria are cultivated in the anaerobic photobioreactor in continuous or batch mode, until a mature photobacteria consortium is developed. Then, the system operates as an autonomous biological reactor without any external energy supply reaching around 95, 98 and 99% of organic matter, nitrogen and phosphorous removal efficiencies, respectively.

The phototrophic biomass culture commonly contained a mixed culture of phototrophic bacteria, including several species of purple non-sulfur bacteria as *Rhodobacter sphaeroides, Rhodopseudomonas palustris* (this two in a dominant position in most of the cases), *Rhodobacter capsulatus, Rhodococcus* sp., *Rhodospirillum rubrum, Rhodospirillum tenue, Rhodocyclus* sp., *Rhodomicrobium* sp., *Rhodopila* sp. and *Rhodoferax* sp. Some purple sulfur bacteria species like *Allochromatium* sp., *Thyocistis* sp., *Thiocapsa* sp. and *Thiococcus* sp. can coexist. Green sulfur bacteria are rarely found, especially in those aqueous off-streams containing high sulfide or thiosulfate concentrations. Additionally, the bacterial consortium can be formed by other non-phototrophic anaerobic or anoxic bacteria that can compete with PPB for organic matter in anaerobic/anoxic conditions operating at high HRT and/or in wastewater containing high concentration of nitrite/nitrate and/or sulfate. PPB absorb photons within the near infrared range (800-1050 nm) and transform the energy of these photons into chemical energy in a light harvesting system, which is mainly composed of a special type of chlorophyll called bacteriochlorophyll (BChl). There are several types of BChl though PPB contain type a and b only, which can absorb photons in the range of 805 and 830-890, and 835-850 and 1020-1040 nm, respectively. The photons are driven into the reaction center of the light harvesting system guided by BChl molecules. Additionally, lower wavelength photons can interact with this system after energy dissipation by other pigments called carotenoids. In any case, once the photons enter the reaction center the light energy is transformed into chemical energy and redox potential. The energy and redox potential are used within the cell for all metabolic purposes. These include nitrogen fixation with concomitant hydrogen production, or hydrogen production alone, and accumulation of poly-phosphate, PHA, glycogen, and other organics.

This invention offers a self-sufficient energy solution for wastewater treatment by coupling the anaerobic photobioreactor and anaerobic digestion of the resulting PPB biomass. COD:N:P ratio has been claimed as a key factor for the long-term operation and efficient nutrients accumulation of this system. With the method of the first aspect of the invention, this ratio can be maintained by circulating the supernatant resulted from the anaerobic biomass digestion, which lead to a long-term stable performance.

Another embodiment of the first aspect of the invention, wherein said biomass cultivated, carried in the biomass outlet line (208, 310) is digested in an anaerobic digester (203, 305).

Another embodiment of the first aspect of the invention, wherein said the phototrophic biomass cultivated is pretreated by hydrolysis methods (303) before entering the anaerobic post-digestion.

Another embodiment of the first aspect of the invention, wherein said hydrolyzed phototrophic biomass is used as nutrients source which can be used as fertilizer or raw material for fertilizers formulation, protein source, and polymers preparation, increasing the sustainability of the system.

Other aspect of the invention provides a method for biomass cultivation, wastewater treatment, nutrients recovery, energy production and high value-added products synthesis by using the anaerobic photobioreactor described above. The method comprises the following steps:

(a) feeding the wastewater stream (205, 307) to the horizontal closed anaerobic ditch (101, 201, 301), (b) exposing the anaerobic phototrophic biomass to light under anaerobic conditions to assimilate organic matter and inorganic nutrients, while PPB biomass is cultivated. Thus, organic contamination contained in wastewater is fully partitioned into the biomass, (c) circulating the wastewater through the anaerobic ditch (101, 201, 301) by means of a covered circulation system (204, 317) to
　(i) improve mixing while minimizing pumping costs
　(ii) cause a natural selection of easily settleable biomass by hydraulic selection pressure, retaining high biomass concentration inside the reactor. This allows an effective treatment, even at high organic loads.

(d) separating the phototrophic biomass from the liquid phase (treated water) by biomass separator (202, 302) where free-living bacteria are washed out from the system (207, 309).

(e) recirculating settleable biomass through a recirculation pipe (210, 318) to control the sludge retention time within the photobioreactor (f) treating the biomass cultured by anaerobic digestion (203, 305) to obtain biogas (211, 319) as energy source (biofuel, heat, electricity).

The main advantages of the present invention are:
a. Cost-competitive and effective biological process for wastewater treatment
b. Easy and rapid start-up procedure, as well as stable long-term performance
c. Self-sufficient and even positive energy balance system
d. Sustainable system characterized by a low carbon footprint and innocuous discharges
e. Simultaneous wastewater treatment, high-value materials recovery and energy production

BRIEF DESCRIPTION OF DRAWINGS

The following Figures are described below. These illustrate the exemplary embodiments and are not limiting their scope.

DESCRIPTION OF EMBODIMENTS

A more detailed description of the embodiments disclosed herein can be obtained by reference to the accompanying drawings. Some descriptive figures are merely schematic representations of the technologies and apparatus and therefore are no intended to describe relative size or dimensions of the components or assemblies thereof.

EXAMPLE 1

Figure 1:
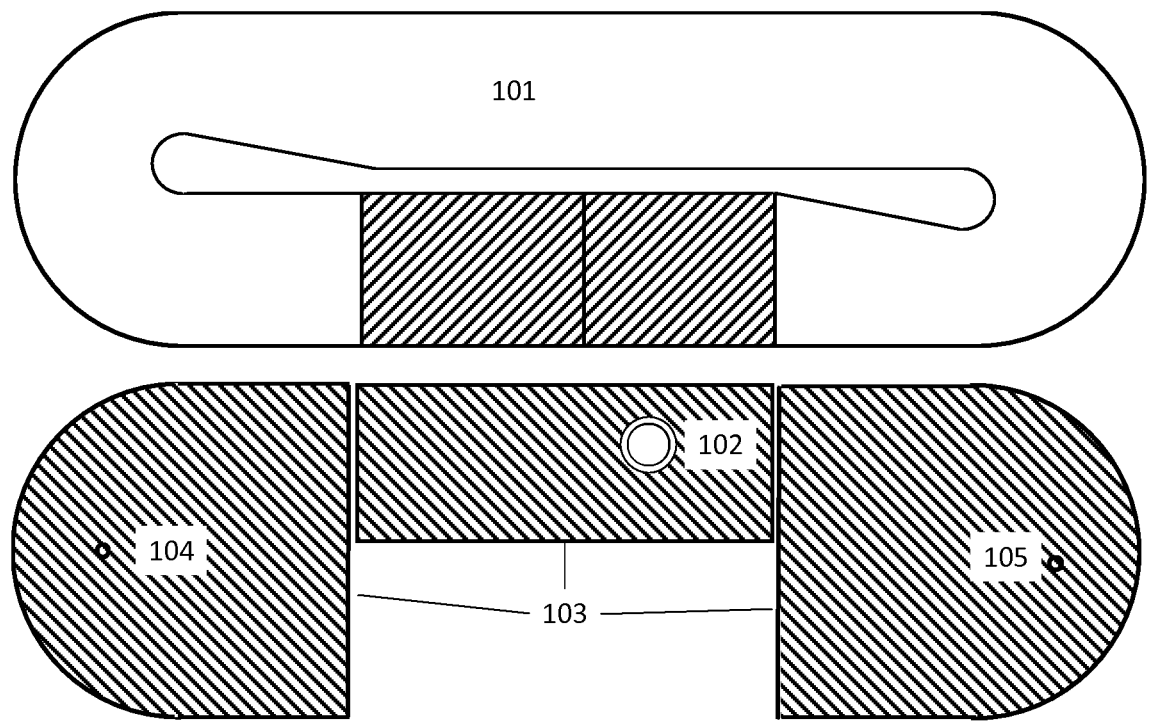
FIG. 1 shows a top view of the photobioreactor and the cover lids.
Figure 2:
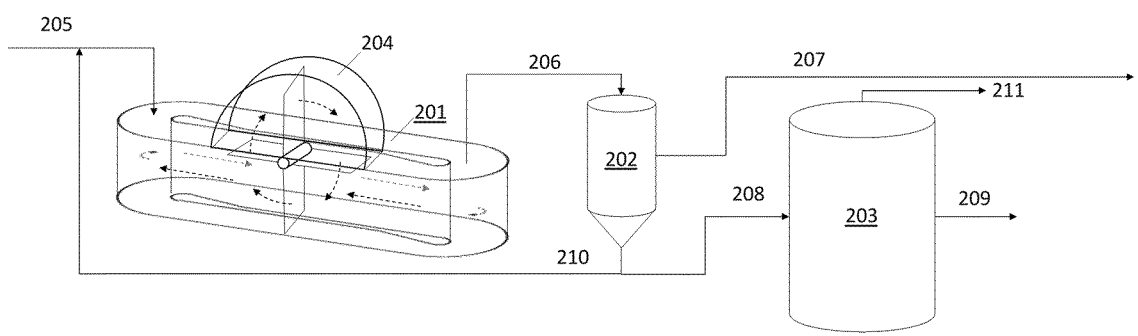
FIG. 2 shows an anaerobic photobioreactor system according to an embodiment of the present invention
Figure 5:
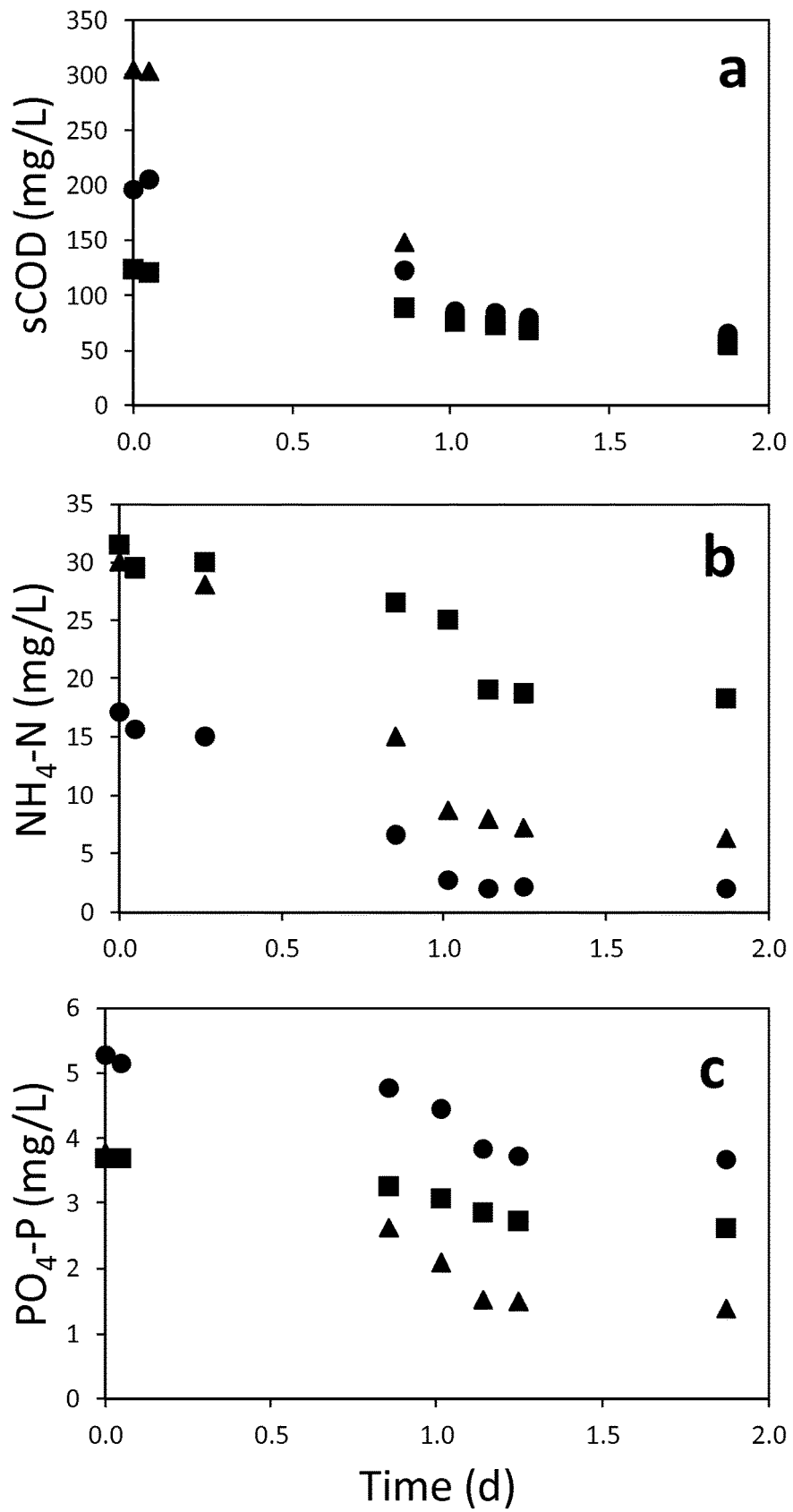
FIG. 5 shows PPB organics and nutrients assimilation experiments examples. Time-course of soluble COD (a), nitrogen (b) and phosphorus (c) in batch tests for wastewater type 1. Experiment id 1 (squares), 2 (circles) and 3 (triangles).
Figure 6:
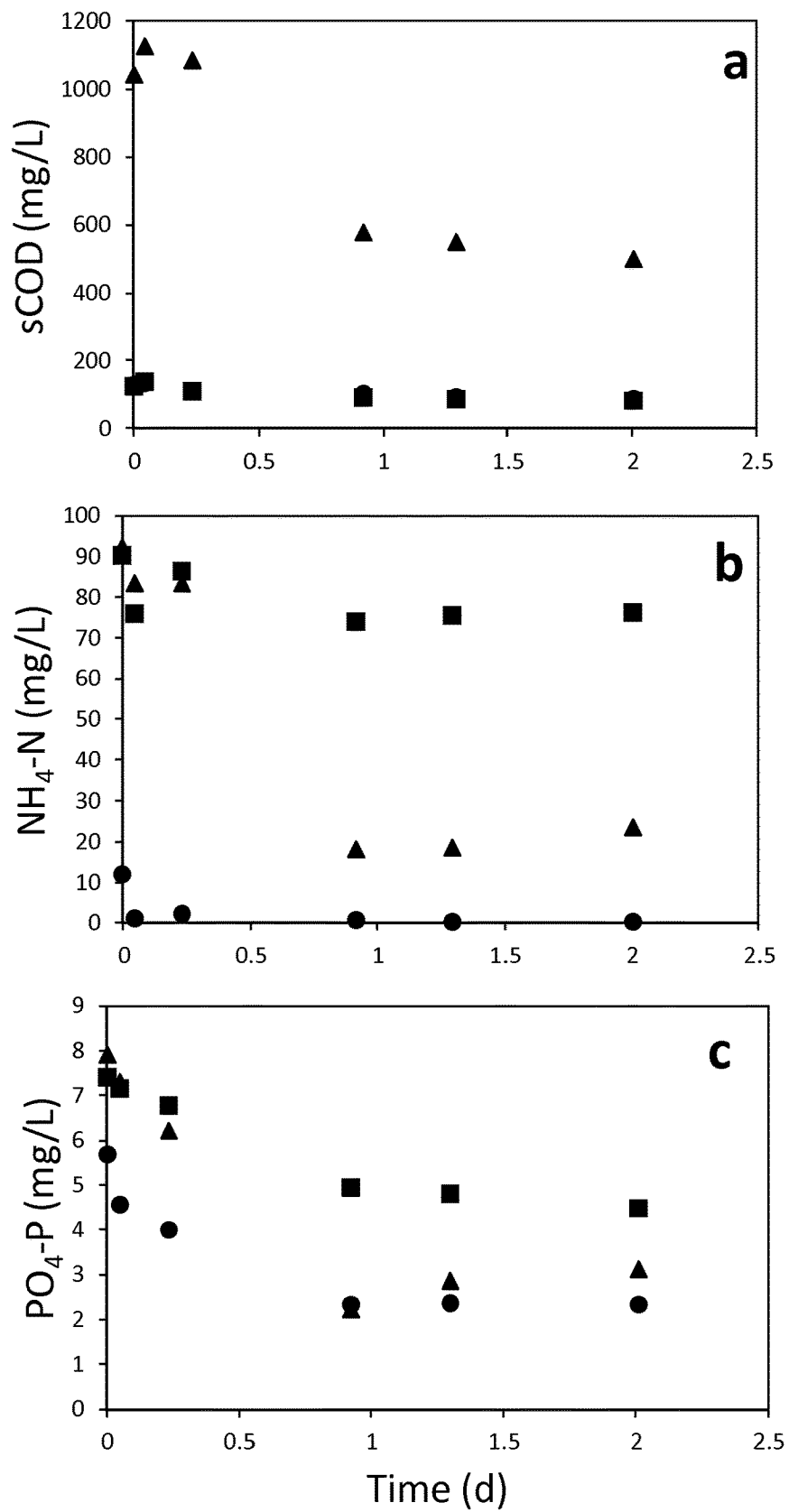
FIG. 6 shows PPB organics and nutrients assimilation experiments examples. Time-course of soluble COD (a), nitrogen (b) and phosphorus (c) in batch tests for wastewater type 2. Experiment id 4 (squares), 5 (circles) and 6 (triangles).

Simultaneous Assimilation of Organic Matter, Nutrients Recovery and Energy Production in Low Strength Wastewater Wastewater with different composition and sources were fed to the system as summarized in Table 1. Feeds are based on two different domestic wastewater containing low (Experiments id 1, 2, 3) and high (Experiments id 4, 5, 6) ammonium concentration. The phototrophic culture was enriched in PPB treating domestic wastewater. In Experiments id 2 and 5, nutrients were removed by precipitation of phosphate with $FeCl_3$ followed by ammonium stripping at pH 9. Experiments id 3 and 6 were carried out with a feed characterized by a COD/N/P ratio of 100/7.5/1.5, which is reported as optimum for PPB growth. The results are shown in FIGS. 5 and 6. These demonstrate that PPB biomass is highly-effective for raw domestic wastewater treatment, and assimilate soluble organics, nitrogen and phosphorus simultaneously. The results indicate that complete assimilation of organics and nutrients can be achieved in a single biological stage, where organics recirculation resulted from the PPB biomass hydrolysis step is an option. Under a suitable COD/N/P ratio, the system is described as in the FIG. 1. If organics recycle is needed to cope with optimum COD/N/P ratios for PPB growth, the system can be upgraded (see FIG. 3).

Figure 3:
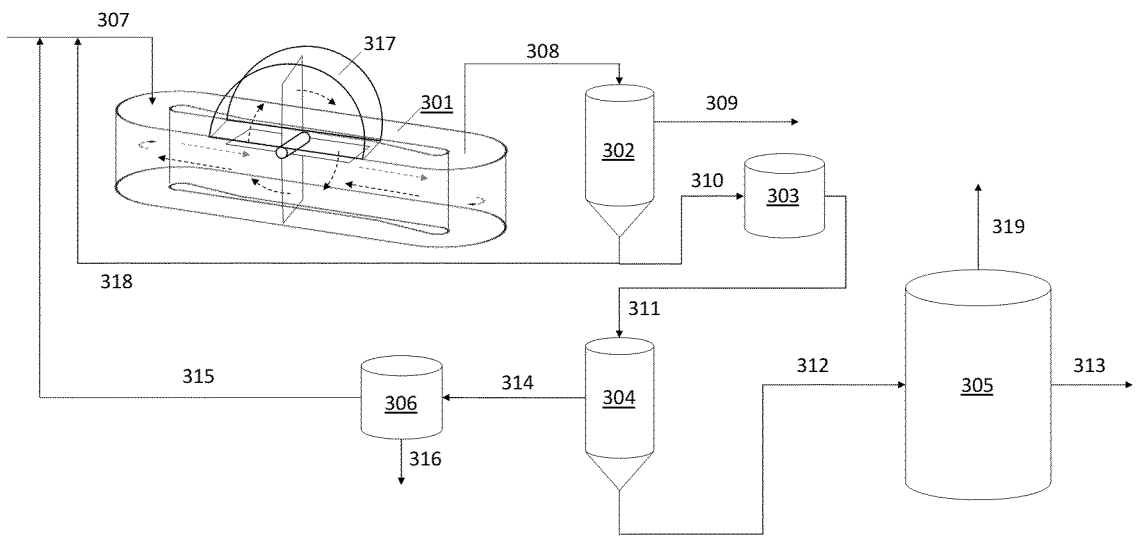
FIG. 3 shows an anaerobic photobioreactor system according to another embodiment of the present invention.

In the present example, reference is made to the elements of FIG. 3.

Stage 1: The anaerobic photobioreactor is a horizontal closed anaerobic ditch (301) fed by wastewater (307). Continuous flow is assessed by inlet and outlet flows (307, 308).

Stage 2: Phototrophic biomass is harvested from the anaerobic photobioreactor by separation systems (302). Purified water exits the system (309). Biomass is recycled through a biomass recirculation pipe (318), thereby maintaining a high biomass concentration inside the covered wastewater system (317) in the anaerobic ditch (301). Ideally, it is suitable up to around 10 gVSS/L.

Stage 3: Biomass collected in an outlet line (208, 310) is harvested and pre-treated (303) to (i) increase degradability and dewaterability, (ii) partially solubilize the organic matter and/or (iii) extract high-value products.

Stage 4: Solid/liquid separation (304) of pre-treated biomass (311), where solid/extracted follows downstream (312) and liquid is returned to the main line (314)

Stage 5: Biofuel (319) production of the collected phototrophic biomass through the anaerobic digester (305). After anaerobic digestion, nutrients are recovered as organic NPK fertilizer (313).

Stage 6: Nutrients recovery (N, P) in the return line (314) by crystallization of struvite (to fully recover P and partial N recovery) and electrodialysis (306) (to collect the remaining N as $NH_4^+$). Solid products are separated (316). Organic liquid phase is recycled into the main line (315) to maintain the COD/N/P ratios.

TABLE 1

Characteristics of wastewater treated in the anaerobic photobioreactors.

| Experiment id | Soluble organic matter as chemical oxygen demand (mg/L) | Nitrogen as $NH_4^+$ (mgN/L) | Phosphorus as $PO_4^{3-}$ (mgP/L) | Total suspended solids (mg/L) | pH |
|---|---|---|---|---|---|
| 1 | 125.0 | 31.5 | 3.7 | 250.0 | 6.5 |
| 2 | 196.0 | 17.0 | 5.3 | 240.0 | 6.5 |
| 3 | 305.0 | 30.0 | 3.8 | 260.0 | 6.5 |
| 4 | 124.0 | 90.0 | 7.4 | 221.0 | 6.5 |
| 5 | 128.5 | 11.9 | 5.7 | 160.0 | 6.4 |
| 6 | 1039.0 | 92.0 | 7.9 | 262.0 | 6.6 |

EXAMPLE 2

Figure 4:
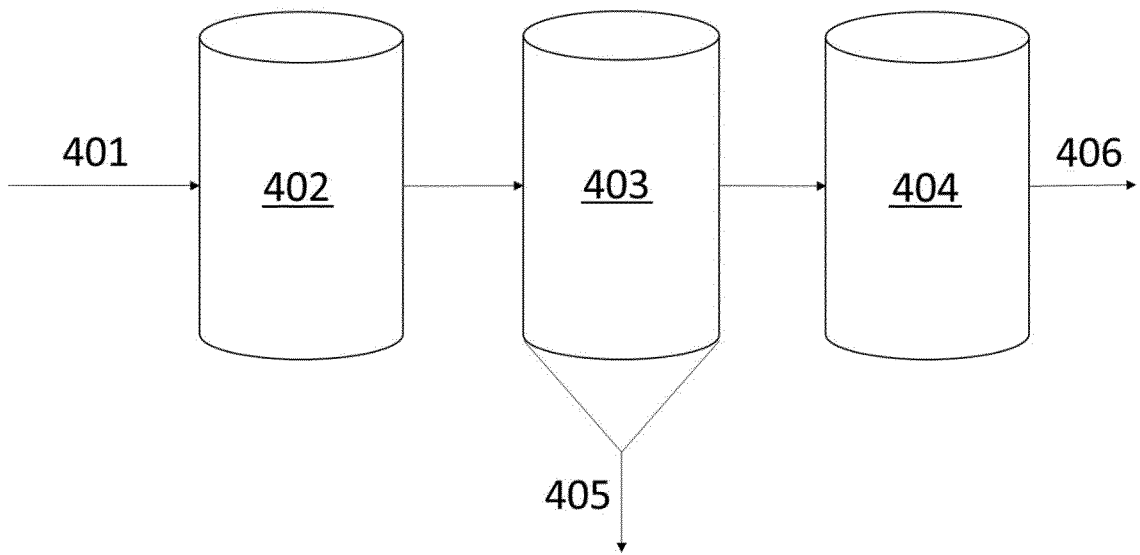
FIG. 4 shows the separation and purification of valuable bioproducts downstream (401), consisting on a extraction stage (402), followed by a separation process (403), where the residue of this process can be anaerobically digested (405), and a final stage of purification (404) to obtain high purity/quality products (406).

Transformation of Organic Matter into High-Value Products in High Strength Wastewater Alternatively, as stated in the description of Stage 3 in example 1, the process can be driven to separation and purification of valuable bioproducts downstream (instead, or in addition, to anaerobic digestion) (FIG. 4), as PHA, single-cell proteins, carotenoids or organic fertilizers. The biomass concentration in the photobioreactor in this case can be up to 10 g/L, therefore artificial illumination is strongly recommended during dark periods or during low sun irradiation. As well as, in this case Stage 5 in example 1 is modified. The sludge line (401) is submitted to extraction (402) of the bioproduct. Bioproduct and remaining biomass are separated by sedimentation or centrifugation (403). The concentrated stream (405) can be submitted to anaerobic digestion (as in the process 305), whereas the stream that contains bioproducts is fed to a subsequent purification step (404), where a purified marketable product is obtained (406).

The Project leading to this application has received funding from the European Union's Horizon 2020 research and innovation program under grant agreement No 685793.

The invention claimed is:

1. An anaerobic photobioreactor for purple phototrophic bacteria (PPB) biomass cultivation, wastewater treatment, nutrients recovery, energy production and high-value products synthesis, comprising:
   a. a horizontal closed anaerobic ditch;
   b. an inlet and an outlet of wastewater, both connected to an internal space of the anaerobic ditch body;
   c. a covered wastewater circulation system inside the anaerobic ditch;
   d. a lid covering the anaerobic ditch to block light at wavelengths below 750 nm, wherein the covering lid is made of poly(methyl methacrylate) with wavelength shifting compounds, wherein the compounds are cyanine dyes selected from the group consisting of 1,1,2-Trimethylbenzindoleninium 1,3-disulfonate, 5-carboxy-1-(4-sulfobutyl)-2,3,3-trimethyl-3H-indolenine 2, and 1-(4-sulfonatobutyl)-2,3,3-trimethylindoleninium-5-sulfonate, or N-Ethyl-2,3,3-trimethylbenzindoleninium 5,7-Disulfonate;
   e. a cylindrical sampling tube submerged into the anaerobic ditch and stuck to the lid, to perform water and biomass analysis and control the headspace pressure;
   f. a settleable biomass recirculation pipe from a biomass separator to the anaerobic ditch; and
   g. a biomass outlet line from the biomass separator.

2. The anaerobic photobioreactor according to claim 1, wherein the photobiorector is lightened with a light source characterized by a wavelength between 750 and 1200 nm.

3. The anaerobic photobioreactor according to claim 2, wherein the light is solar irradiation.

4. The anaerobic photobioreactor according to claim 1, wherein a reactor headspace is connected to a gas exit, wherein biohydrogen produced by photofermentation is collected.

5. The anaerobic photobioreactor according to claim 1, wherein said headspace is connected to a $N_2$ source to sparge the reactor.

6. The anaerobic photobioreactor according to claim 1, further comprising an anaerobic post-treatment in an anaerobic digester of the biomass cultivated, carried in the biomass outlet line.

7. The anaerobic photobioreactor according to claim 1, wherein said biomass outlet line is connected to a hydrolysis pre-treatment.

8. The anaerobic photobioreactor according to claim 1, wherein a sludge line exit from hydrolysis pre-treatment is connected to a downstream process to produce biopolymers, proteins or organic fertilizers.

9. Method for biomass cultivation, wastewater treatment, nutrients recovery, energy production and high-value products synthesis wherein the method is carried out using the anaerobic photobioreactor recited in claim 1, comprising:
   (a) feeding the wastewater stream to the horizontal closed anaerobic ditch;
   (b) exposing the anaerobic phototrophic biomass to light under anaerobic conditions to assimilate organic matter and inorganic nutrients, while PPB biomass is cultivated;
   (c) circulating the wastewater through the anaerobic ditch by means of a covered circulation system;
   (d) separating the phototrophic biomass from the liquid phase by biomass separator where free-living bacteria are washed out from the system;
   (e) recirculating settleable biomass through a recirculation pipe to control the sludge retention time within the photobioreactor; and
   (f) treating the biomass cultured by anaerobic digestion to obtain biogas as energy source.

* * * * *